(12) United States Patent
Yeum

(10) Patent No.: US 10,184,899 B2
(45) Date of Patent: Jan. 22, 2019

(54) VEHICLE PART INSPECTION DEVICE

(71) Applicant: Hyundai Motor Company, Seoul (KR)

(72) Inventor: Jung Whan Yeum, Seoul (KR)

(73) Assignee: Hyundai Motor Company, Seoul (KR)

( * ) Notice: Subject to any disclaimer, the term of this patent is extended or adjusted under 35 U.S.C. 154(b) by 115 days.

(21) Appl. No.: 15/383,066

(22) Filed: Dec. 19, 2016

(65) Prior Publication Data

US 2018/0059029 A1 Mar. 1, 2018

(30) Foreign Application Priority Data

Sep. 1, 2016 (KR) .................. 10-2016-0112724

(51) Int. Cl.
*G01N 21/88* (2006.01)
*G01N 21/95* (2006.01)

(52) U.S. Cl.
CPC ..... *G01N 21/8851* (2013.01); *G01N 21/8806* (2013.01); *G01N 21/95* (2013.01); *G01N 2201/06113* (2013.01)

(58) Field of Classification Search
CPC ................................................. G01N 21/8851
See application file for complete search history.

(56) References Cited

U.S. PATENT DOCUMENTS

| 3,890,552 A * | 6/1975 | Devol ................... B25J 9/0084 318/568.14 |
| 4,076,131 A * | 2/1978 | Dahlstrom ............... B25J 9/046 414/730 |
| 4,715,709 A * | 12/1987 | Sekine ............... G01N 21/9515 250/559.48 |
| 5,722,104 A * | 3/1998 | Wentworth ............. B60S 3/066 15/53.2 |
| 5,997,670 A * | 12/1999 | Walter ................ B29C 63/0056 150/166 |
| 8,054,459 B2 * | 11/2011 | Lindner ................. G01N 21/94 356/241.1 |

FOREIGN PATENT DOCUMENTS

| KR | 10-2012-0063773 A | 6/2012 |
| KR | 10-2013-0061334 A | 6/2013 |
| KR | 10-2015-0007535 A | 1/2015 |

* cited by examiner

*Primary Examiner* — Tri T Ton
*Assistant Examiner* — Rebecca C Bryant
(74) *Attorney, Agent, or Firm* — Mintz Levin Cohn Ferris Glovsky and Popeo, P.C.; Peter F. Corless

(57) ABSTRACT

A vehicle part inspection device is configured to inspect an inspection object secured on a jig frame by a securing unit, and may include: i) a sensing unit which is pivotably installed on a mount frame, moves in multi-axis directions along the jig frame, and senses an inspection portion of the inspection object; and ii) angle changing units which are installed to be radially connected with the sensing unit, and change a sensing angle of the sensing unit by applying forward and rearward operating force to the sensing unit.

12 Claims, 9 Drawing Sheets

100

(a)

(b)

VEHICLE PART INSPECTION DEVICE

CROSS-REFERENCE TO RELATED APPLICATION

This application claims under 35 U.S.C. § 119(a) the benefit of Korean Patent Application No. 10-2016-0112724 filed in the Korean Intellectual Property Office on Sep. 1, 2016, the entire contents of which are incorporated herein by reference.

BACKGROUND

(a) Technical Field

The present disclosure relates to a vehicle part inspection device, and more particularly, to a vehicle part inspection device for inspecting moving components such as a door assembly during an assembly process.

(b) Description of the Related Art

In general, a vehicle manufacturer produces a vehicle by combining thousands of components in several assembly processes for mass production.

For example, among moving parts that constitute the vehicle, a door assembly includes an inner panel and an outer panel, and has a structure in which the inner panel and the outer panel are assembled by hemming.

Meanwhile, the quality of front and rear door assemblies of the vehicle are important with respect to the appearance of the vehicle. In particular, intervals, level differences, and external appearance waviness of the door assembly are important factors that may impact the external appearance quality of the vehicle.

Therefore, during a design process included in the process of assembling the vehicle, various types of assembling parts such as hemming parts of the door assembly are inspected prior to mounting the door assembly on a vehicle body to ensure high quality thereof.

During the process of inspecting the door assembly, the assembled parts of the door assembly are subjected to a visual inspection by using a vision inspection device in a state in which the door assembly is secured by a securing unit.

The aforementioned inspection device is difficult to be applied in common to door assemblies having different shapes and sizes in accordance with different types of vehicles, and as a result, the door assemblies are inspected by inspection devices dedicated for respective types of vehicles and items.

However, in the related art, dedicated inspection devices, which correspond to the door assemblies of the different types of vehicles, are required, which causes a disadvantage in view of flexibly producing different types of vehicles, and causes an increase in investment costs, because further costs are required to remodel and newly manufacture door inspection equipment when the vehicle part inspection device is applied to new types of vehicles.

Meanwhile, in the related art, the inspection device is mounted on a multi-articulated robot, such as a 6-axis robot. Also, the inspection device is moved and rotated to an optimum inspection position by moving and rotating a robot arm, such that an external appearance quality of an inspection object such as the door assembly is inspected by the inspection device.

However, in a case in which the external appearance quality of the inspection object is inspected by moving and rotating the inspection device by using the multi-articulated robot as described above, the inspection device is difficult to move and rotate at a high speed, and there may occur an interference with peripheral equipment when the robot is moved.

The above information disclosed in this Background section is only for enhancement of understanding of the background of the disclosure and therefore it may contain information that does not form the prior art that is already known in this country to a person of ordinary skill in the art.

SUMMARY

The present disclosure provides a vehicle part inspection device capable of being used in common to inspect the external appearance quality of inspection objects having different shapes and sizes in accordance with the types of vehicles.

The present disclosure also provides a vehicle part inspection device which may achieve, with a simple configuration, high-speed movement and rotation of an inspection device for inspecting an inspection object, and does not cause the occurrence of interference with peripheral equipment.

An exemplary embodiment of the present disclosure provides a vehicle part inspection device for inspecting an inspection object secured on a jig frame by a securing unit, the vehicle part inspection device including: i) a sensing unit which is pivotably installed on a mount frame, moves in multi-axis directions along the jig frame, and senses an inspection portion of the inspection object; and ii) angle changing units which are installed to be radially connected with the sensing unit, and change a sensing angle of the sensing unit by applying forward and rearward operating force to the sensing unit.

In addition, in the vehicle part inspection device according to the exemplary embodiment of the present disclosure, the sensing unit may be pivotably connected to a center point of the mount frame by a main spring.

In addition, in the vehicle part inspection device according to the exemplary embodiment of the present disclosure, the sensing unit may include three stem rods disposed radially.

In addition, in the vehicle part inspection device according to the exemplary embodiment of the present disclosure, the angle changing units may be connected with the respective stem rods by sub springs.

In addition, in the vehicle part inspection device according to the exemplary embodiment of the present disclosure, the angle changing units may apply the forward and rearward operating force to the respective stem rods while converting rotational motion of servo motors into rectilinear motion.

Another exemplary embodiment of the present disclosure provides a vehicle part inspection device for inspecting an inspection object secured on a jig frame by a securing unit, the vehicle part inspection device including: i) a movable member which is installed on the jig frame so as to be movable in multi-axis directions; ii) a mount frame which is fixedly installed on the movable member; iii) a sensing unit which is pivotably installed on the mount frame, and senses an inspection portion of the inspection object; and iv) angle changing units which are radially connected to the sensing unit, elastically support the sensing unit, apply forward and rearward operating force to the sensing unit, and change a sensing angle of the sensing unit.

In addition, in the vehicle part inspection device according to the exemplary embodiment of the present disclosure, the mount frame may include: a main frame which is connected with the movable member, and supports the sensing unit; and sub frames which are radially connected with the main frame based on a center of the main frame, and support the angle changing units.

In addition, in the vehicle part inspection device according to the exemplary embodiment of the present disclosure, the sensing unit may include: a center rod which is pivotably connected to a center point of the mount frame by a main spring; three stem rods which are radially connected with the center rod with the center rod disposed at the center; and a sensing body which is installed to be connected to the center rod.

In addition, in the vehicle part inspection device according to the exemplary embodiment of the present disclosure, the sensing unit may include: a line laser emitting unit which is installed on the sensing body, and emits line laser to the inspection portion of the inspection object; and a vision camera which is installed on the sensing body, captures a vision image of the inspection portion of the inspection object, and outputs the vision data to a controller.

In addition, in the vehicle part inspection device according to the exemplary embodiment of the present disclosure, the angle changing units may be installed to be connected with the respective stem rods by sub springs.

In addition, in the vehicle part inspection device according to the exemplary embodiment of the present disclosure, the angle changing unit may include: a servo motor which is mounted on the mount frame; and a power transmission unit which is installed to be connected with the servo motor, connected with the stem rods by the sub springs, and converts rotational motion of the servo motor into rectilinear motion.

In addition, in the vehicle part inspection device according to the exemplary embodiment of the present disclosure, the movable member may be installed to be reciprocally movable in a front and rear direction of the jig frame by a first drive unit.

In addition, in the vehicle part inspection device according to the exemplary embodiment of the present disclosure, the movable member may be installed to be reciprocally movable in a left and right direction of the jig frame by a second drive unit.

In addition, in the vehicle part inspection device according to the exemplary embodiment of the present disclosure, the movable member may be installed to be reciprocally movable in an up and down direction of the jig frame by a third drive unit.

Yet another exemplary embodiment of the present disclosure provides a vehicle part inspection device for inspecting an inspection object secured on a jig frame by a securing unit, the vehicle part inspection device including: i) a movable member which is installed on the jig frame so as to be movable in multi-axis directions; ii) a mount frame which is fixedly installed on the movable member; iii) a main body which is installed at a center point of the mount frame so as to be pivotable by a main spring; iv) a sensing body which is fixedly installed on the main body, and senses an inspection portion of the inspection object; and v) angle changing units which are radially connected with the main body by sub springs, apply forward and rearward operating force to the sensing body, and change a sensing angle of the sensing body.

In addition, in the vehicle part inspection device according to the exemplary embodiment of the present disclosure, the main body may include: a center rod which is pivotably connected to a center point of the mount frame by the main spring; and a plurality of stem rods which is radially connected to the center rod, and connected with the angle changing units by the sub springs.

In addition, in the vehicle part inspection device according to the exemplary embodiment of the present disclosure, the stem rods may be disposed at an interval of 120 degrees in a circular circumferential direction of the center rod with the center rod disposed at the center.

In addition, in the vehicle part inspection device according to the exemplary embodiment of the present disclosure, a line laser emitting unit, which emits line laser to the inspection portion of the inspection object, and a vision camera, which captures a vision image of the inspection portion of the inspection object and outputs the vision data to a controller, may be installed on the sensing body.

In addition, in the vehicle part inspection device according to the exemplary embodiment of the present disclosure, a lighting unit, which emits illumination light to the inspection portion of the inspection object, may be installed on the sensing body.

In addition, in the vehicle part inspection device according to the exemplary embodiment of the present disclosure, the angle changing unit may include: a servo motor which is mounted on the mount frame; and a power transmission unit which is installed to be connected with the servo motor, connected with the stem rods by the sub springs, and converts rotational motion of the servo motor into rectilinear motion.

In addition, in the vehicle part inspection device according to the exemplary embodiment of the present disclosure, a fixing bracket, which fixes one end of the sub spring, may be installed on the stem rod.

In addition, in the vehicle part inspection device according to the exemplary embodiment of the present disclosure, the power transmission unit may include: a lead screw which is connected to a driving shaft of the servo motor; and a moving bracket which is fixed to the other end of the sub spring, screw-coupled to the lead screw, and rectilinearly moved by the rotation of the lead screw.

In addition, in the vehicle part inspection device according to the exemplary embodiment of the present disclosure, when the moving bracket is rectilinearly moved to the servo motor by the rotation of the lead screw, the main body may change a sensing angle of the sensing body by rotating in the movement direction of the moving bracket.

According to the exemplary embodiments of the present disclosure, since the sensing angle of the sensing unit may be changed to a desired direction by the angle changing units, it is possible to inspect in common the external appearance quality of the inspection objects having shapes and sizes different depending on the types of vehicles.

Therefore, in the exemplary embodiment of the present disclosure, it is possible to improve flexibility in view of producing various types of vehicles, and to reduce additional investment costs incurred when remodeling and newly manufacturing the inspection equipment when the vehicle part inspection device is applied to new types of vehicles.

Further, in the exemplary embodiment of the present disclosure, the movable member may be moved in multi-axis directions at a high speed and the sensing angle of the sensing unit may be changed at a high speed by the angle changing units, and as a result, it is possible to further improve efficiency in respect to inspection of the vehicle parts, and to prevent interference with peripheral equipment unlike the related art using a robot.

BRIEF DESCRIPTION OF THE DRAWINGS

The drawings are intended to be used as references for describing the exemplary embodiments of the present disclosure, and the accompanying drawings should not be construed as limiting the technical spirit of the present disclosure.

DETAILED DESCRIPTION OF THE EMBODIMENTS

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Throughout the specification, unless explicitly described to the contrary, the word "comprise" and variations such as "comprises" or "comprising" will be understood to imply the inclusion of stated elements but not the exclusion of any other elements. In addition, the terms "unit", "-er", "-or", and "module" described in the specification mean units for processing at least one function and operation, and can be implemented by hardware components or software components and combinations thereof.

Further, the control logic of the present disclosure may be embodied as non-transitory computer readable media on a computer readable medium containing executable program instructions executed by a processor, controller or the like. Examples of computer readable media include, but are not limited to, ROM, RAM, compact disc (CD)-ROMs, magnetic tapes, floppy disks, flash drives, smart cards and optical data storage devices. The computer readable medium can also be distributed in network coupled computer systems so that the computer readable media is stored and executed in a distributed fashion, e.g., by a telematics server or a Controller Area Network (CAN).

The present disclosure will be described more fully hereinafter with reference to the accompanying drawings, in which exemplary embodiments of the disclosure are shown. As those skilled in the art would realize, the described embodiments may be modified in various different ways, all without departing from the spirit or scope of the present disclosure.

Figure 1:
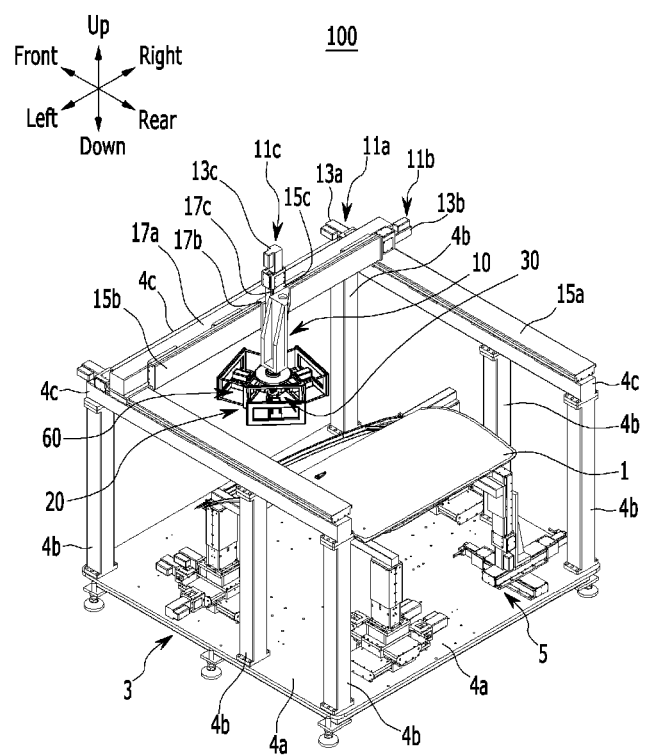
FIG. 1 is a perspective view illustrating an example in which a vehicle part inspection device according to an exemplary embodiment of the present disclosure is applied.

FIG. 1 is a perspective view illustrating an example in which a vehicle part inspection device according to an exemplary embodiment of the present disclosure is applied.

Referring to FIG. 1, a vehicle part inspection device 100 according to an exemplary embodiment of the present disclosure may be applied to an inspection process of inspecting the external appearance quality of various types of vehicle parts during a design process among processes of assembling vehicles.

For example, the vehicle part inspection device 100 according to the exemplary embodiment of the present disclosure may be applied to a moving part inspection process of inspecting an external appearance quality of an inspection object 1 such as a door assembly as a vehicle part.

That is, the exemplary embodiment of the present disclosure may be applied to a door inspection process of inspecting assembled portions (inspection portions) of the door assembly prior to loading the door assembly to a door mounting process.

However, the scope of the present disclosure should not be construed as being necessarily limited to the process of inspecting the external appearance quality of the moving part for a vehicle such as the door assembly, and the technical spirit of the present disclosure may be applied as long as the vehicle part inspection device inspects vehicle parts which are mounted in the vehicle body and used for various types of purposes.

The vehicle part inspection device 100 according to the exemplary embodiment of the present disclosure has a structure capable of inspecting in common the external appearance quality of the inspection objects 1 having different shapes and sizes in accordance with the types of vehicles.

In addition, the exemplary embodiment of the present disclosure provides the vehicle part inspection device 100 which may achieve, with a simple configuration, high-speed movement and rotation of the vehicle part inspection device 100 for inspecting the inspection object 1, and does not cause the occurrence of interference with peripheral equipment.

Meanwhile, the vehicle part inspection device 100 according to the exemplary embodiment of the present disclosure is configured to inspect the external appearance quality of the inspection object 1 secured on a jig frame 3 by a securing unit 5, and the vehicle part inspection device 100 may inspect an assembled portion of the inspection object 1 by moving the inspection object 1 in multi-axis directions on the jig frame 3.

In the exemplary embodiment of the present disclosure, reference directions are not set to LTH directions (a width direction of the vehicle body, a longitudinal direction of the vehicle body, and a height direction of the vehicle body) which are widely known in the art, but set to a front and rear direction, a left and right direction, and an up and down direction based on the jig frame 3.

The jig frame 3 is a frame on which various types of constituent elements to be described below are mounted, and the jig frame 3 includes accessory elements such as a bracket, a plate, a housing, a case, a block, and a collar which are used for supporting the constituent elements.

However, the accessory elements are used to install the respective constituent elements on the jig frame 3, and in the exemplary embodiment of the present disclosure, the accessory elements are commonly called the jig frame 3 as provided herein.

Here, the jig frame 3 includes a base frame 4a which is a quadrangular frame, a plurality of vertical frames 4b which is disposed in the up and down direction at corner portions and edge portions at both left and right sides of the base frame 4a, and a plurality of horizontal frames 4c which is connected to upper ends of the vertical frames 4b.

The horizontal frames 4c connect the vertical frames 4b at both left and right sides at a front side of the base frame 4a, and connect the vertical frames 4b at both front and rear sides at both left and right sides of the base frame 4a. That is, a portion between the vertical frames 4b at both left and right sides at a rear side of the base frame 4a is opened in a state in which the vertical frames 4b are not connected by the horizontal frame 4c. The reason is to easily load the inspection object 1 to the securing unit 5 on the base frame 4a.

Further, the securing unit 5 is installed on an upper surface of the base frame 4a, and serves to align the inspection object 1 at a preset position and fix the inspection object 1. The securing unit 5 includes various types of support means which support the inspection object 1 by moving in the multi-axis directions while corresponding to the inspection objects 1 different depending on the types of vehicles, and various types of clamping means which clamp the inspection object 1 by moving in the multi-axis directions.

Because the securing unit 5 is configured as a securing device having publicly known support means and clamping means which may align a predetermined component at a position and fix the position of the predetermined component, a further detailed description of the configuration of the securing unit 5 will be omitted in the present specification.

Figure 2:
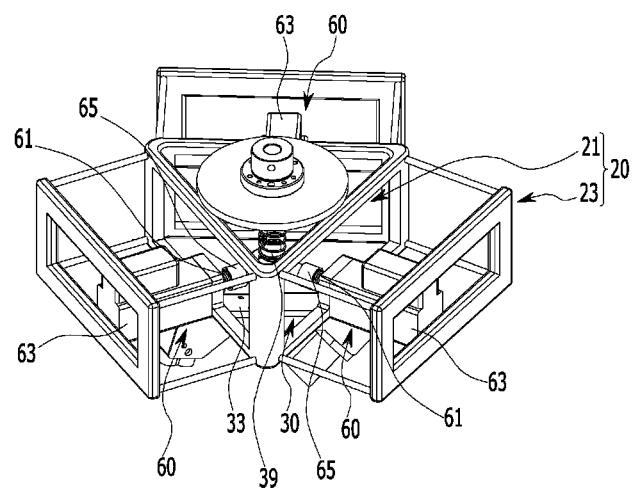
FIGS. 2 and 3 are perspective views illustrating the vehicle part inspection device according to the exemplary embodiment of the present disclosure.
Figure 3:
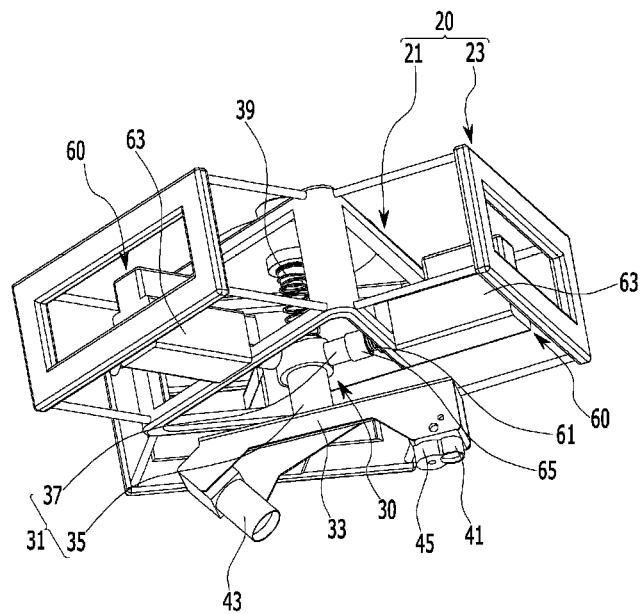

FIGS. 2 and 3 are perspective views illustrating the vehicle part inspection device according to the exemplary embodiment of the present disclosure.

Referring to FIGS. 1 to 3, the vehicle part inspection device 100 according to the exemplary embodiment of the present disclosure basically includes a movable member 10, a mount frame 20, a sensing unit 30, and angle changing units 60.

In the exemplary embodiment of the present disclosure, the movable member 10 is installed on the jig frame 3 so as to be reciprocally movable in the multi-axis directions (the front and rear, left and right, and up and down directions). The mount frame 20, the sensing unit 30, and the angle changing units 60, which will be described below, are mounted on the movable member 10.

The movable member 10 is installed on the horizontal frame 4c of the jig frame 3 so as to be reciprocally movable in the front and rear, left and right, and up and down directions by first to third drive units 11a, 11b, and 11c.

The first drive unit 11a includes a first movable body 17a which is reciprocally moved in the front and rear direction along the horizontal frames 4c by a first guide structure 15a which converts rotational force of a first motor 13a into rectilinear motion.

The second drive unit 11b includes a second movable body 17b which is reciprocally moved in the left and right direction along the first movable body 17a by a second guide structure 15b which converts rotational force of a second motor 13b to rectilinear motion.

Further, the third drive unit 11c includes a third movable body 17c which is reciprocally moved in the up and down direction on the second movable body 17b by a third guide structure 15c which converts rotational force of the third motor 13c into rectilinear motion. The movable member 10 according to the exemplary embodiment of the present disclosure is installed on the third movable body 17c.

The guide structures 15a, 15b, and 15c have lead (or ball) screws, guide rails, and the like of the publicly known technology which convert the rotational force of the motors 13a, 13b, and 13c into rectilinear motion.

In the exemplary embodiment of the present disclosure, the mount frame 20 serves to install the sensing unit 30 and the angle changing units 60 which will be described below, and the mount frame 20 includes various types of accessory elements such as a bracket, a plate, a rib, and a block for supporting the constituent elements.

The mount frame 20 is fixedly installed on the movable member 10. The mount frame 20 includes a main frame 21 and sub frames 23. The main frame 21 is connected directly with the movable member 10, and supports the sensing unit 30 to be described below. For example, the main frame 21 is formed in a triangular frame shape.

Further, the sub frames 23 are radially connected to the main frame 21 with the main frame 21 disposed at a center, and support the angle changing units 60 to be described below. For example, the sub frames 23 are integrally connected to respective sides of the main frame 21.

In the exemplary embodiment of the present disclosure, the sensing unit 30 is moved in the front and rear, left and right, and up and down directions of the jig frame 3 by the movable member 10, and inspects the inspection portion (assembled portion) of the inspection object 1 secured by the securing unit 5. That is, the sensing unit 30 serves to obtain data information associated with the inspection portion of the inspection object 1.

Figure 4:
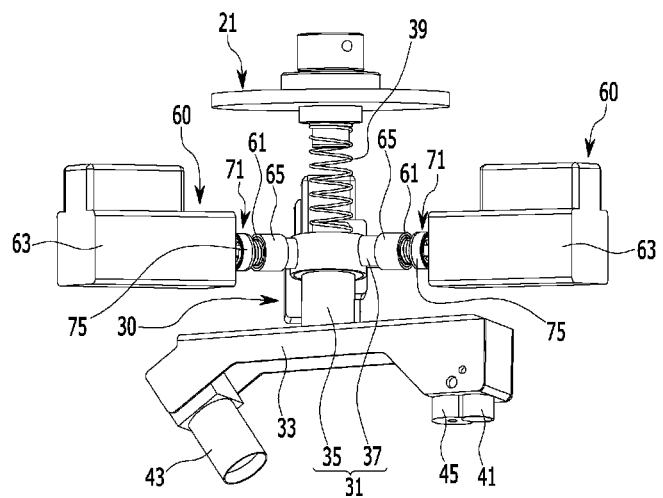
FIG. 4 is a front configuration diagram illustrating a sensing unit and angle changing units that are applied to the vehicle part inspection device according to the exemplary embodiment of the present disclosure.
Figure 5:
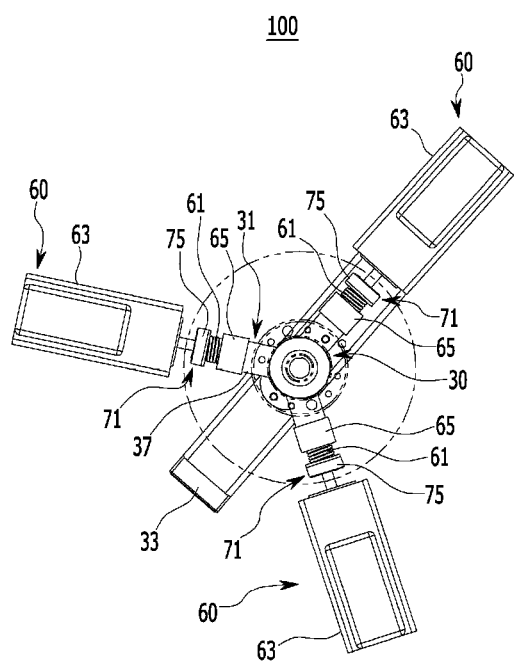
FIG. 5 is a top plan configuration diagram illustrating the sensing unit and the angle changing units that are applied to the vehicle part inspection device according to the exemplary embodiment of the present disclosure.

FIG. 4 is a front configuration diagram illustrating the sensing unit applied to the vehicle part inspection device according to the exemplary embodiment of the present disclosure, and FIG. 5 is a top plan configuration diagram illustrating the sensing unit applied to the vehicle part inspection device according to the exemplary embodiment of the present disclosure.

Referring to FIGS. 2 to 5, in the exemplary embodiment of the present disclosure, the sensing unit 30 is pivotably installed on the mount frame 20. The sensing unit 30 is pivotably connected to a center point of the mount frame 20 by a main spring 39.

The sensing unit 30 includes a main body 31 and a sensing body 33. The main body 31 is pivotably installed at the center point of the main frame 21 of the mount frame 20 by the main spring 39.

The main body 31 includes a center rod 35 and stem rods 37. The center rod 35 is pivotably connected to the center point of the main frame 21 by the main spring 39. The center rod 35 is disposed in the up and down direction based on the drawings, and an upper end of the center rod 35 is connected to the center point of the main frame 21 by the main spring 39.

Here, the main spring 39 has a preset elastic force, and preferably is provided as a pivotable coil spring, and one end (an upper end in the drawing) of the main spring 39 is connected to the center point of the main frame 21 by a fixing plate, and the other end (a lower end in the drawing) of the main spring 39 is fixed to the upper end of the center rod 35.

A plurality of stem rods 37 is provided and radially connected to the center rod 35. Three stem rods 37 are radially connected to the center rod 35 with the center rod 35 disposed at the center. The stem rods 37 are disposed at an interval of 120 degrees along a circular circumferential direction of the center rod 35 with the center rod 35 disposed at the center.

The sensing body 33 serves to substantially sense the inspection portion (assembled portion) of the inspection object 1, and is fixedly installed on the main body 31. The sensing body 33 is fixedly installed at a lower end of the center rod 35 of the main body 31.

The sensing body 33 has a line laser emitting unit 41 and a vision camera 43. The line laser emitting unit 41 is used to measure a width, a height, and the like of the inspection portion. The line laser emitting unit 41 emits line laser, which is oscillated by a laser oscillator (non-illustrated in the drawings), to the inspection portion of the inspection object 1.

The vision camera 43 captures a vision image of the inspection portion of the inspection object 1, and outputs the vision data to a controller (not illustrated in the drawings). The vision camera 43 captures a vision image of the inspection portion of the inspection object 1 and a vision image of a profile of the line laser which is emitted to the inspection portion from the line laser emitting unit 41, and outputs the vision data to the controller.

The controller may calculate the width and the height of the inspection portion based on the vision data associated with a surface of the inspection portion and the line laser which is provided from the vision camera 43, analyze and compare the calculated values with preset reference values, and detect whether the inspection portion has a defect.

For example, the controller may detect a short-circuit, deflection, depression, a height defect, and the like of the inspection portion based on the vision data associated with the surface of the inspection portion and the line laser which is provided from the vision camera 43.

Further, a lighting unit 45, which emits illumination light to the inspection portion of the inspection object 1, is installed on the sensing body 33. The lighting unit 45 provides a sufficient light amount to the inspection portion.

Referring to FIGS. 2 to 5, in the exemplary embodiment of the present disclosure, the angle changing units 60 elastically support the sensing unit 30, apply forward and rearward operating force to the sensing unit 30, and change a sensing angle of the sensing unit 30 with respect to the inspection portion of the inspection object 1. That is, the angle changing units 60 may change the sensing angle of the sensing body 33 by applying forward and rearward operating force to the main body 31.

The angle changing units 60 are installed to be radially connected with the sensing unit 30, and radially connected with the main body 31 by sub springs 61. The angle changing units 60 are connected with the respective stem rods 37 of the main body 31 by the sub springs 61. Here, the angle changing units 60 convert rotational motion of the motors into rectilinear motion, and may apply the forward and rearward operating force to the respective stem rods 37 of the main body 31.

Figure 6:
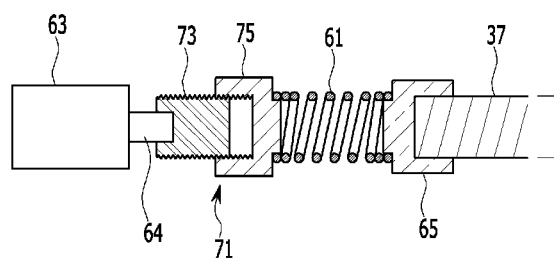
FIG. 6 is a cross-sectional configuration diagram illustrating the angle changing units applied to the vehicle part inspection device according to the exemplary embodiment of the present disclosure.

As illustrated in FIG. 6, each of the angle changing units 60 includes a servo motor 63 and a power transmission unit 71. The servo motor 63 is a motor which easily controls a rotational speed and a rotation angle thereof, and three servo motors 63 are provided to correspond to the respective stem rods 37 of the main body 31, and fixedly installed on the sub frames 23 of the mount frame 20.

The power transmission unit 71 converts the rotational motion of the servo motor 63 into rectilinear motion, and applies the forward and rearward operating force to the respective stem rods 37 of the main body 31. The power transmission unit 71 is installed to be connected with the servo motor 63, and connected with the respective stem rods 37 by the sub springs 61.

Here, the sub spring 61 is provided as a compressive coil spring having preset elastic force, and elastically connects the power transmission unit 71 and the stem rod 37. One end of the sub spring 61 is fixed to an end portion of the stem rod 37, and a fixing bracket 65, which fixes one end of the sub spring 61, is installed at an end portion of the stem rod 37. One end of the sub spring 61 is integrally connected with the fixing bracket 65 by welding.

The power transmission unit 71 includes a lead screw 73 and a moving bracket 75. The lead screw 73 is connected with a driving shaft 64 of the servo motor 63. The moving bracket 75 is rectilinearly moved by the rotation of the lead screw 73, and the moving bracket 75 is fixed to the other end of the sub spring 61 and screw-coupled to the lead screw 73. The other end of the sub spring 61 is integrally connected with the moving bracket 75 by welding.

Screw threads, which are screw-coupled to the lead screw 73, are formed on an inner circumferential surface of the moving bracket 75. The moving bracket 75 is rectilinearly moved in a longitudinal direction of the lead screw 73 as the lead screw 73 is rotated by the servo motor 63.

Hereinafter, an operation and an operational effect of the vehicle part inspection device 100 according to the exemplary embodiment of the present disclosure, which is configured as described above, will be described in detail with reference to the aforementioned drawings and the attached drawings.

Figure 7:
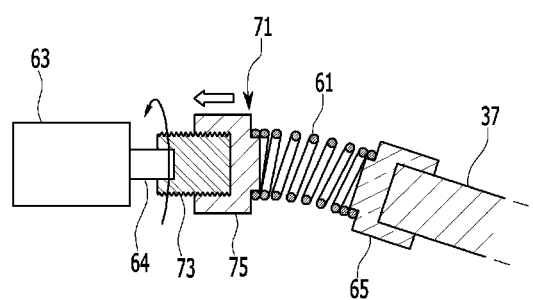
FIGS. 7 to 9 are views for explaining an operation of the vehicle part inspection device according to the exemplary embodiment of the present disclosure.
Figure 8:
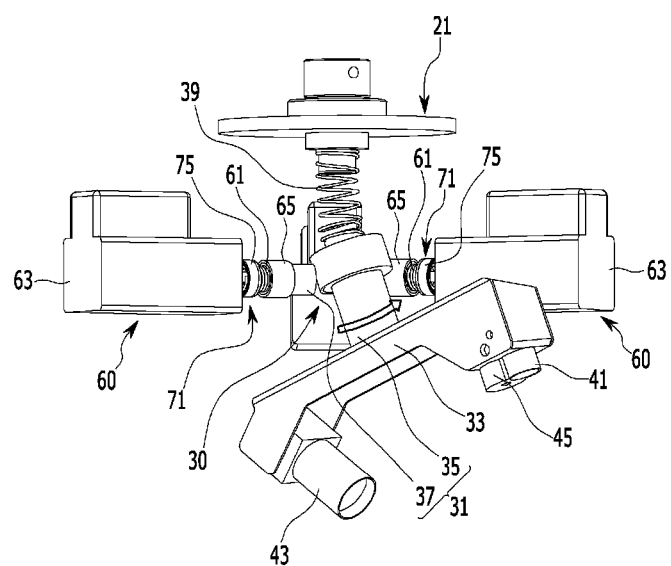
Figure 9:
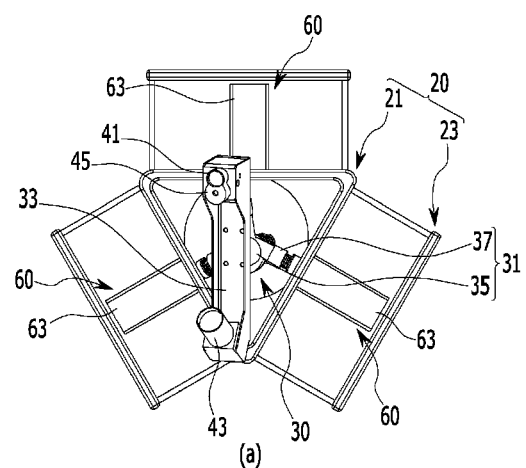
Figure 9:
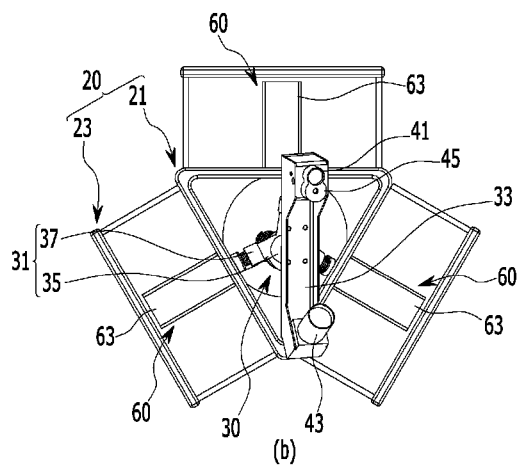

FIGS. 7 to 9 are views for explaining an operation of the vehicle part inspection device according to the exemplary embodiment of the present disclosure.

First, in the exemplary embodiment of the present disclosure, the inspection object 1 such as the door assembly is loaded to the securing unit 5 on the jig frame 3. Then, the securing unit 5 accurately positions the inspection object 1 at a preset position by the support means, and fixes the inspection object 1 by the clamping means.

In this state, in the exemplary embodiment of the present disclosure, the movable member 10 is moved in the front and rear, left and right, and up and down directions by the first to third drive units 11a, 11b, and 11c, and the sensing body 33 of the sensing unit 30 is positioned corresponding to the inspection portion of the inspection object 1.

Then, in the exemplary embodiment of the present disclosure, the movable member 10 is moved in the front and rear, left and right, and up and down directions by the first to third drive units 11a, 11b, and 11c, and the inspection portion (assembled portion) of the inspection object 1 is inspected by the line laser emitting unit 41 and the vision camera 43 of the sensing body 33.

In the exemplary embodiment of the present disclosure, during the process of inspecting the inspection portion by moving the sensing body 33 in accordance with the inspection portion of the inspection object 1 by using the movable member 10, it is necessary to change the sensing angle of the sensing body 33 in accordance with the shape of the inspection portion. Therefore, in the exemplary embodiment of the present disclosure, as illustrated in FIG. 7, the servo motor 63 of the angle changing unit 60 is rotated in one direction.

Then, the lead screw 73 is rotated in one direction by the driving shaft 64 of the servo motor 63, and the moving bracket 75 screw-coupled to the lead screw 73 is moved toward the servo motor 63 according to the exemplary embodiment of the present disclosure.

As the moving bracket 75 is moved in one direction as described above, the moving bracket 75 pulls the main body 31 of the sensing unit 30 which is connected with the moving bracket 75 by the sub spring 61. That is, the moving bracket 75 pulls the stem rod 37 of the main body 31 through the sub spring 61.

Then, as illustrated in FIG. 8, the main body 31 is rotated in the movement direction of the moving bracket 75 through the main spring 39 connected with the center rod 35 in a state in which the main body 31 is elastically supported by the sub springs 61 that connects the remaining stem rods 37 and the remaining moving brackets 75.

Therefore, in the exemplary embodiment of the present disclosure, the sensing body 33 fixed to the center rod 35 of the main body 31 is rotated in one direction about the center point of the main frame 21, and as a result, the sensing angle of the sensing body 33 may be changed.

Further, in the exemplary embodiment of the present disclosure, when the lead screw 73 is rotated in the opposite direction by the servo motor 63, the moving bracket 75 is moved to the original position, and the main body 31 of the sensing unit 30 may be moved to the original position.

Therefore, in the exemplary embodiment of the present disclosure, as illustrated in FIG. 9, the sensing angle of the sensing body 33 may be changed in a desired direction by selectively operating the servo motors 63 of the angle changing units 60. Here, the sensing angle of the sensing body 33 may be freely changed in accordance with the number of rotations of the motors.

Meanwhile, in the exemplary embodiment of the present disclosure, the line laser emitting unit 41 of the sensing body 33 emits the line laser to the inspection portion of the inspection object 1. At the same time, in the exemplary embodiment of the present disclosure, the lighting unit 45 of the sensing body 33 emits illumination light to the inspection portion, and the vision camera 43 captures a vision image of the surface of the inspection portion and a vision image of the line laser emitted to the inspection portion from the line laser emitting unit 41, and then outputs the vision data to the controller.

Therefore, the controller calculates the width and the height of the inspection portion based on the vision data associated with a surface of the inspection portion and the line laser which is provided from the vision camera 43, analyzes and compares the calculated values with preset reference values, and detects whether the inspection portion has a defect.

According to the vehicle part inspection device 100 according to the exemplary embodiment of the present disclosure which has been described above, since the sensing angle of the sensing unit 30 may be changed to a desired direction by the angle changing units 60, it is possible to inspect in common the external appearance quality of the inspection objects 1 having shapes and sizes different depending on the types of vehicles.

Therefore, in the exemplary embodiment of the present disclosure, it is possible to improve flexibility in view of producing various types of vehicles, and to reduce additional investment costs incurred when remodeling and newly manufacturing the inspection equipment when the vehicle part inspection device is applied to new types of vehicles.

Further, in the exemplary embodiment of the present disclosure, the movable member 10 may be moved in the multi-axis directions at a high speed and the sensing angle of the sensing unit 30 may be changed at a high speed by the angle changing units 60, and as a result, it is possible to further improve efficiency in respect of inspection of the vehicle parts, and to prevent interference with peripheral equipment unlike the related art using a robot.

While this disclosure has been described in connection with what is presently considered to be practical exemplary embodiments, it is to be understood that the disclosure is not limited to the disclosed embodiments, but, on the contrary, is intended to cover various modifications and equivalent arrangements included within the spirit and scope of the appended claims.

What is claimed is:

1. A vehicle part inspection device for inspecting an inspection object secured on a jig frame by a securing unit, the vehicle part inspection device comprising:
    a sensing unit which is pivotably installed on a mount frame, moves in multi-axis directions along the jig frame, and senses an inspection portion of the inspection object; and
    angle changing units which are installed to be radially connected with the sensing unit, and change a sensing angle of the sensing unit by applying forward and rearward operating force to the sensing unit,
    wherein the sensing unit includes three stem rods disposed radially, and the angle changing units are connected with the respective stem rods by sub springs,
    wherein the angle changing units apply the forward and rearward operating force to the respective stem rods while converting rotational motion of servo motors into rectilinear motion,
    wherein the angle changing unit includes:
        a servo motor which is mounted on the mount frame; and
        a power transmission unit which is installed to be connected with the servo motor, connected with the stem rods by the sub springs, and converts rotational motion of the servo motor into rectilinear motion, and
    wherein the power transmission unit includes:
        a lead screw which is connected to a driving shaft of the servo motor; and
        a moving bracket which is fixed to the other end of the sub spring, screw-coupled to the lead screw, and rectilinearly moved by the rotation of the lead screw.

2. The vehicle part inspection device of claim 1, wherein: the sensing unit is pivotably connected to a center point of the mount frame by a main spring.

3. A vehicle part inspection device for inspecting an inspection object secured on a jig frame by a securing unit, the vehicle part inspection device comprising:
    a movable member which is installed on the jig frame so as to be movable in multi-axis directions;
    a mount frame which is fixedly installed on the movable member;

a sensing unit which is pivotably installed on the mount frame, and senses an inspection portion of the inspection object; and angle changing units which are radially connected to the sensing unit, elastically support the sensing unit, apply forward and rearward operating force to the sensing unit, and change a sensing angle of the sensing unit, wherein the sensing unit includes:
   a center rod which is pivotably connected to a center point of the mount frame by a main spring;
   three stem rods which are radially connected with the center rod with the center rod disposed at the center; and
   a sensing body which is installed to be connected to the center rod, wherein the angle changing units are installed to be connected with the respective stem rods by sub springs, wherein the angle changing unit includes:
   a servo motor which is mounted on the mount frame; and
   a power transmission unit which is installed to be connected with the servo motor, connected with the stem rods by the sub springs, and converts rotational motion of the servo motor into rectilinear motion, and wherein the power transmission unit includes:
   a lead screw which is connected to a driving shaft of the servo motor; and
   a moving bracket with is fixed to the other end of the sub spring, screw-coupled to the lead screw, and rectilinearly moved by the rotation of the lead screw.

4. The vehicle part inspection device of claim 3, wherein the mount frame includes:
   a main frame which is connected with the movable member, and supports the sensing unit; and
   sub frames which are radially connected with the main frame based on a center of the main frame, and support the angle changing units.

5. The vehicle part inspection device of claim 3, wherein the sensing unit includes:
   a line laser emitting unit which is installed on the sensing body, and emits line laser to the inspection portion of the inspection object; and
   a vision camera which is installed on the sensing body, captures a vision image of the inspection portion of the inspection object, and outputs the vision data to a controller.

6. The vehicle part inspection device of claim 3, wherein the movable member is installed to be reciprocally movable in a front and rear direction of the jig frame by a first drive unit, is installed to be reciprocally movable in a left and right direction of the jig frame by a second drive unit, and is installed to be reciprocally movable in an up and down direction of the jig frame by a third drive unit.

7. A vehicle part inspection device for inspecting an inspection object secured on a jig frame by a securing unit, the vehicle part inspection device comprising:
   a movable member which is installed on the jig frame so as to be movable in multi-axis directions;
   a mount frame which is fixedly installed on the movable member;
   a main body which is installed at a center point of the mount frame so as to be pivotable by a main spring;
   a sensing body which is fixedly installed on the main body, and senses an inspection portion of the inspection object; and
   angle changing units which are radially connected with the main body by sub springs, apply forward and rearward operating force to the sensing body, and change a sensing angle of the sensing body, wherein the main body includes:
   a center rod which is pivotably connected to a center point of the mount frame by the main spring; and
   a plurality of stem rods which is radially connected to the center rod, and connected with the angle changing units by the sub springs, wherein the angle changing unit includes:
   a servo motor which is mounted on the mount frame; and
   a power transmission unit which is installed to be connected with the servo motor, connected with the stem rods by the sub springs, and converts rotational motion of the servo motor into rectilinear motion, and wherein the power transmission unit includes:
   a lead screw which is connected to a driving shaft of the servo motor; and
   a moving bracket with is fixed to the other end of the sub spring, screw-coupled to the lead screw, and rectilinearly moved by the rotation of the lead screw.

8. The vehicle part inspection device of claim 7, wherein:
   the stem rods are disposed at an interval of 120 degrees in a circular circumferential direction of the center rod with the center rod disposed at the center.

9. The vehicle part inspection device of claim 7, wherein:
   a line laser emitting unit, which emits line laser to the inspection portion of the inspection object, and a vision camera, which captures a vision image of the inspection portion of the inspection object and outputs the vision data to a controller, are installed on the sensing body.

10. The vehicle part inspection device of claim 9, wherein:
   a lighting unit, which emits illumination light to the inspection portion of the inspection object, is installed on the sensing body.

11. The vehicle part inspection device of claim 7, wherein:
   a fixing bracket, which fixes one end of the sub spring, is installed on the stem rod.

12. The vehicle part inspection device of claim 7, wherein:
   when the moving bracket is rectilinearly moved to the servo motor by the rotation of the lead screw,
   the main body changes a sensing angle of the sensing body by rotating in the movement direction of the moving bracket.

* * * * *